July 4, 1944. A. R. GOLDSBY ET AL Re. 22,510
ALKYLATION OF HYDROCARBONS
Original Filed June 18, 1938
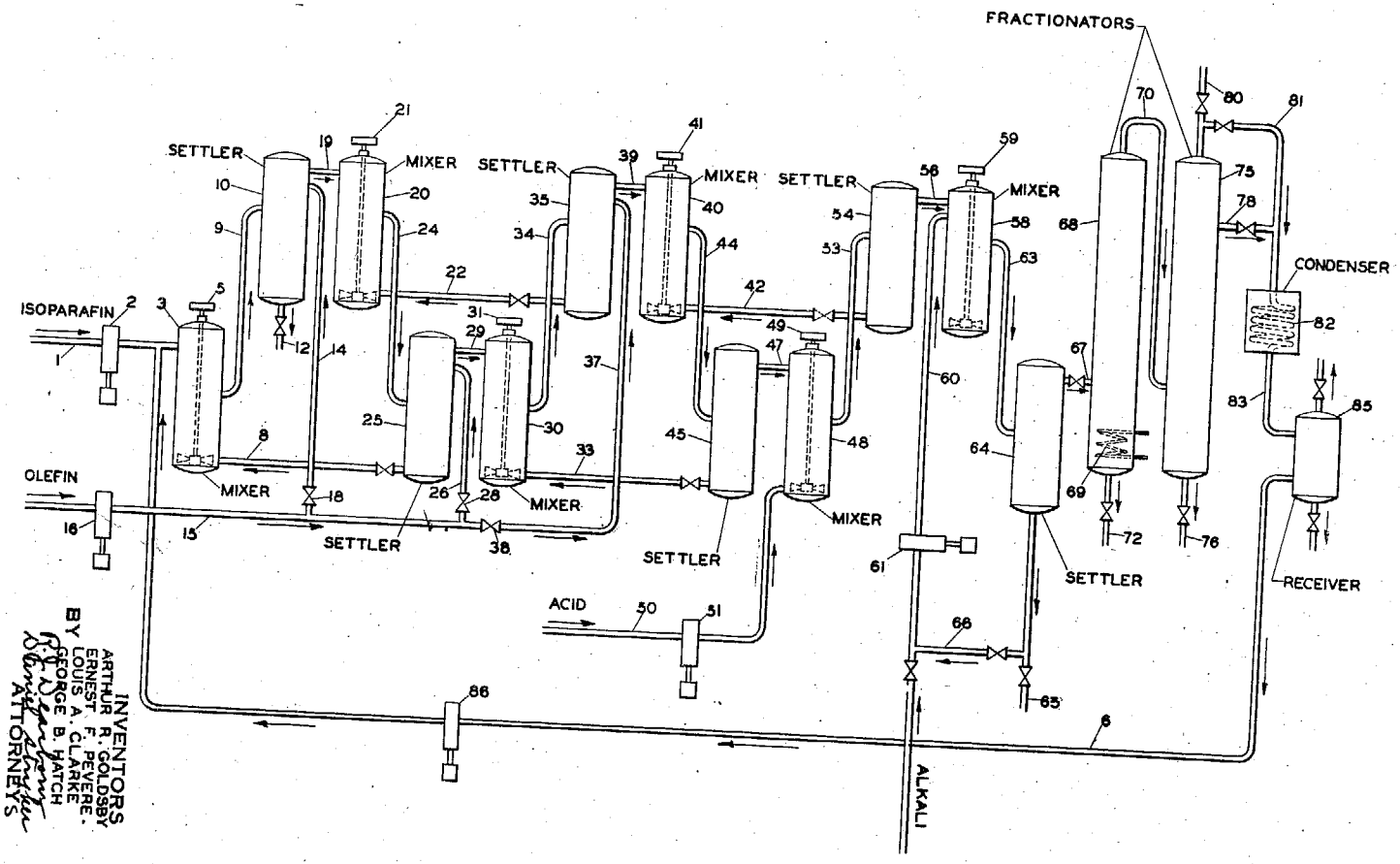
INVENTORS
ARTHUR R. GOLDSBY
ERNEST F. PEVERE
LOUIS A. CLARKE
GEORGE B. HATCH
BY R. J. Dearborn
Daniel Starkey
ATTORNEYS Reissued July 4, 1944

Re. 22,510

UNITED STATES PATENT OFFICE 22,510

ALKYLATION OF HYDROCARBONS

Arthur R. Goldsby and Ernest F. Pevere, Beacon, Louis A. Clarke, Fishkill, and George B. Hatch, Beacon, N. Y., assignors, by mesne assignments, to The Texas Company, New York, N. Y., a corporation of Delaware Original No. 2,256,450, dated September 16, 1941, Serial No. 214,488, June 18, 1938. Application for reissue September 24, 1941, Serial No. 412,166

7 Claims. (Cl. 260—683.4)

This invention relates to the alkylation of hydrocarbons and has to do with a process for the reaction of certain paraffin hydrocarbons with olefins to produce saturated hydrocarbons of high antiknock value, suitable for the manufacture of motor fuel.

More particularly the present invention is an improvement in the method for the alkylation of isoparaffins with olefins in the presence of sulfuric acid as the catalyst. The invention is particularly applicable to the alkylation of lower boiling isoparaffins, such as isobutane and isopentane, with normally gaseous olefins, including cracking still gases or a fraction thereof such as a fraction containing predominantly $C_4$ hydrocarbons or $C_3$ hydrocarbons or a mixture of $C_3$ and $C_4$ hydrocarbons; propylene; isomeric normal butenes; isobutylene, or polymers thereof, for example, di-isobutylene and tri-isobutylene; or co-polymers resulting from the polymerization of one molecule of normal butene with one molecule of isobutylene.

In the alkylation of isoparaffins with olefins using sulfuric acid as a catalyst, it is customary to contact the mixture of olefin and isoparaffin with the acid under such conditions that alkylation of the isoparaffins with the olefin occurs to produce branch chain, saturated hydrocarbons. In a continuous type of operation, wherein a stream of hydrocarbons is charged to the system and a stream of spent or partially spent sulfuric acid is withdrawn, there may be a substantial amount of olefins absorbed by the acid and lost or removed from the system with the withdrawn used acid. The loss of olefins in the used acid is particularly observed when the reaction is carried out in a preferred type of continuous multi-stage countercurrent operation wherein the used acid immediately before withdrawal from the system is ordinarily contacted with the fresh hydrocarbon charge and tends to absorb olefins therefrom.

In accordance with the present invention, the used acid, before withdrawal from the alkylation system, is treated with the isoparaffin to strip the acid of its olefin content. Although not restricting the invention to any particular theory of reaction, it is believed that the olefins absorbed by the acid alkylate the isoparaffin, which is in relatively high ratio to the olefins, during the stripping operation. As applied to a countercurrent flow type of operation, the stripping of the used acid may take place in one or more additional stages wherein only the isoparaffin, which may be the stream of isoparaffin charging stock, is contacted with the used acid.

As applied to a countercurrent type of operation using a multiple injection of the olefins between stages in a multi-stage operation, the olefins according to the invention may be injected into the hydrocarbon layer of the settlers, whereby the olefins are mixed with the reaction products containing a high proportion of isoparaffin to effect dilution of the olefins before contacting the mixture with the acid catalyst in a subsequent mixer.

The invention will be mode fully understood from the following description read in connection with the accompanying drawing, which shows diagrammatically a sketch of one form of apparatus for carrying out the process of the invention. In the drawing, there is shown a five-stage countercurrent system, but the number of stages may vary, and it is to be understood that that part of the invention, insofar as it relates broadly to the isoparaffin stripping of the used acid, is applicable to other systems for carrying out the herein described type of alkylation operation.

Referring to the drawing, the isoparaffin charging stock is introduced by the line 1 and pump 2 into a mixer 3 which is provided with a stirring mechanism 5. The charging stock may be mixed with additional isoparaffin, recycled in the system through the line 6, as explained more fully hereinafter. In the mixer 3, the isoparaffin is intimately contacted with used acid, which may be spent or partially spent, introduced through the line 8. The acid may contain a substantial amount of absorbed olefins and it is intended that the acid be stripped of these olefins by contact with the isoparaffin in the mixer 3. Due to the high ratio of isoparaffin, favorable conditions are provided for the alkylation of the isoparaffin by the olefins. The acid and hydrocarbon mixture is transferred from the mixer 3 through the line 9 to a settler 10, wherein the stripped acid separates from the hydrocarbons and collects in the lower portion of the settler and may be withdrawn through the valve controlled line 12. The mixer 3 and settler 10 comprise the acid stripping stage, wherein only isoparaffins are contacted with the used acid. While only one stage of acid stripping is shown, it is to be understood that any number may be used.

The hydrocarbons collect in the upper portion of the settler 10 and into this hydrocarbon layer is introduced a portion of the olefin charge by line 14 which communicates with the olefin charging line 15 containing a pump 16. By suitable adjustment of the valve 18 in the line 14, any portion of the olefin charge may be introduced into the hydrocarbon layer in the upper portion of the settler 10. The olefins introduced through the line 14 commingle with the hydrocarbons in the settler and are diluted thereby to produce a mixture containing a high proportion of isoparaffin to olefins, which is favorable for obtaining the alkylation reaction. Ordinarily the proportion of olefin introduced through the line 15 and the isoparaffin introduced through the line 1, are such as to give an overall ratio of isoparaffin to olefin of at least 1:1 and preferably from about 3:1 to 5:1. The olefin charge is ordinarily split between a number of stages, and one skilled in the art will be able to split the olefin charge to introduce the desired amount into each stage. Ordinarily the proportions introduced in the various stages are about equal and in case the olefin charge is split between three stages, approximately one-third should be introduced through the line 14 into the settler 10.

The hydrocarbon mixture is transferred from the upper portion of the settler 10 through the line 19 to a mixer 20, provided with a stirring mechanism 21. In the mixer 20, the mixture of isoparaffin and olefins is intimately contacted with partially spent acid introduced into the lower portion of the mixer through the line 22. The reaction products are withdrawn from the mixer 20 through the line 24 and introduced into a settler 25. In this settler the acid and hydrocarbons stratify and the lower acid layer is conducted from the settler through the valve controlled line 8 to the mixer 3, referred to heretofore. Into the upper hydrocarbon layer of the settler 25 is introduced additional olefin through the line 26 which communicates with the olefin charging line 15. By suitable regulation of the valve 28 in the line 26, any proportion of the olefin charge may be commingled with the hydrocarbon layer in the settler 25.

The hydrocarbon mixture is transferred from the settler 25 through the line 29 to a mixer 30 provided with a stirring mechanism 31. In the mixer 30, the hydrocarbons are contacted with sulfuric acid catalyst, comprising partially spent sulfuric acid introduced through the line 33. The reaction mixture is conducted from the mixer 30 through the line 34 to a settler 35 wherein the separation of acid and hydrocarbon is allowed to take place. The acid layer collecting in the bottom is allowed to flow through the valve controlled line 22 to the mixer 20, referred to heretofore. Additional olefin is injected into the hydrocarbon layer of settler 35, by means of the line 37 which communicates with the olefin charging line 15, whereby a portion of olefin may be introduced into settler 35 by regulation of the valve 38 in the line 37.

The hydrocarbon mixture is transferred from the settler 35 through the line 39 to a mixer 40 provided with a stirrer 41 which intimately mixes the hydrocarbon with the partially spent acid introduced into the mixer through the line 42. The reaction mixture from the mixer 40 is passed through the line 44 to a settler 45 wherein the acid separates as a lower layer from the hydrocarbons and is withdrawn through the valve controlled line 33 to the mixer 30, referred to heretofore. The hydrocarbon layer collected in the upper portion of the settler 45 is transferred through the line 47 to a mixer 48, provided with stirrer 49. While there is shown no injection of olefin into the hydrocarbon layer in the settler 45, it is to be understood that such injection may be used if desired. The final mixer 48 provides an opportunity for effecting reaction of substantially all the remaining olefin with the isoparaffin.

The acid introduced into the mixer 48 is fresh or new acid, which should be about 93 to 100% or more concentration, or preferably about 94 to 98%. This acid, which may be new or restored acid, is introduced through the line 50 by pump 51. The amount of acid introduced is sufficient to make the overall ratio of acid to olefin charge about 1:1 or less and preferably about .5 to .8:1. The reaction mixture is transferred from the mixer 48 through the line 53 to a settler 54. The acid and hydrocarbon separate in the settler 54 and the acid collecting in the lower layer of the settler is conducted through the valve controlled line 42 to the mixer 40, referred to heretofore. The hydrocarbons are passed from the upper portion of the settler 54 through the line 56 to a mixer 58 provided with a stirrer 59.

In the mixer 58 the hydrocarbons are intimately contacted with a neutralizing reagent, such as an aqueous alkaline solution, for example dilute caustic solution, introduced through the line 60 by the pump 61. The mixture of neutralizing reagent and hydrocarbon is passed through the line 63 to a settler 64 wherein the neutralizing reagent settles out and may be withdrawn from the lower portion of the settler through the valve controlled line 65 or any portion thereof recycled to the mixer 58 through the branch line 66, which communicates with the line 60. The neutralized hydrocarbons are transferred from the settler 64 through the valve controlled line 67 to fractionator 68. The fractionator 68 is provided with suitable heating means, such as heating coil 69, whereby substantially all hydrocarbons within the motor fuel boiling range and lower are vaporized and removed overhead through the vapor line 70. The bottoms of higher boiling point than the desired motor fuel may be withdrawn from the lower portion of the fractionator through the line 72.

The overhead vapors removed through the vapor line 70 are introduced into the secondary fractionator or stabilizer 75, wherein a separation is made between the desired motor fuel and lighter hydrocarbons, such as the normally gaseous hydrocarbons. The motor fuel fraction is withdrawn from the lower portion of the fractionator 75 through the valve controlled line 76. This motor fuel may be a stable or unstable product falling within the boiling range of gasoline or a normally liquid hydrocarbon fraction of high antiknock value, suitable for blending with gasoline.

The operation of the fractionator 75 may vary considerably, but it is intended to make a separation of a fraction relatively rich in isobutane for recycling to the system. If a portion or all of the normal butane is retained in the gasoline which is drawn from the lower portion of the fractionator, the remaining products may be fractionated to obtain an isobutane cut which may be withdrawn as a side stream through the valve controlled line 78, and the lighter hydrocarbons released from the upper portion of the fractionator through the valve controlled line 80. The nature of the products discharged through the line 80 will, of course, depend somewhat on the character of the charging stock.

For example, if the charging stock is a cracked fraction containing $C_4$ hydrocarbons and lighter, the gases discharged through the line 80 may comprise $C_3$ hydrocarbons and lighter. If the charging stock is essentially $C_4$ hydrocarbons, then the overhead product from the fractionator 75 may comprise essentially isobutane, which may be taken overhead through the line 81 instead of the line 78.

In case a portion or all of the normal butane is separated from the gasoline fraction withdrawn from the lower portion of the fractionator 75 through the line 76, then it may be desirable to separate a $C_4$ fraction from the fractionator 75 and subject this fraction to further fractionation in another fractionator, not shown, to separate the isobutane from the normal butane. In either case, the isobutane from the line 78 or 81 is passed through a condenser coil 82 wherein it is condensed and the condensate passed through the run-down line 83 to receiver 85. Any portion of the isobutane collecting in the receiver 85 may be passed through the line 6 containing a pump 86 to the mixer 3, referred to heretofore.

The reaction taking place in the system described is ordinarily in the liquid phase. Sufficient pressure is maintained on the hydrocarbons to maintain them in the liquid phase and this pressure will vary from atmospheric to substantial superatmospheric pressure, depending on the temperatures employed. The temperature may vary from 0 to 125° F. or higher, and preferably about 60 to 90° F. At these temperatures the pressures may vary from 0 to about 100 pounds or more, and preferably about 25 to 50 pounds. Sufficient time is provided to obtain substantially complete reaction of the olefins in the alkylation of the isoparaffins. Ordinarily the time would be about 30 to 90 minutes, and preferably 40 to 60 minutes.

As an example of the operation of the invention, the following data were obtained on a five-stage counterflow apparatus, using as the isoparaffin charging stock a fraction containing about 98% isobutane, and as the olefin charging stock plant gas which was a topped stabilizer reflux containing about 45% $C_4$ olefins, and about 24% isobutane. The isobutane was contacted with the used acid in the first stage and the plant gas was split and injected into the second and third stages.

| | |
|---|---|
| Charge to Stage No. 1 | Isobutane |
| Charge to stage No. 2 | Plant gas |
| Charge to stage No. 3 | Plant gas |
| Concentration of sulfuric acid—per cent | 98 |
| Acid/olefin ratio | 1.18 |
| Isobutane/olefin ratio | 3.75 |
| Temperature, °F | 60.8 |
| Contact time—minutes | 90 |
| Percent sulfuric acid in recovered acid | 94.4 |
| 311 °F. fraction: | |
| Percent yield by weight basis of olefin | 146.2 |
| Octane number CFRM | 91.6 |
| Bromine number | 1 |
| 311–400 °F. fraction: | |
| Percent yield by weight basis of olefin | 19.1 |
| Bromine number | 1 |

It will be observed from the above results that using an isobutane stripping stage in which the spent acid prior to withdrawal from the system was contacted with the isobutane charge only, the yield of 311 end point product was approximately 146%. Also, the recovered acid was of good quality and had a concentration of 94.4%.

The treatment of the used acid with isoparaffin may be used advantageously in connection with any suitable system, including countercurrent or concurrent operation, in which the acid is recycled. In such a case the recycle acid and isoparaffin may be contacted in a separate reactor, for example the initial reactor, and the olefin charged to one or more successive reactors.

The present invention has the advantage of producing increased yields of the desired products and increased acid concentration which permits the use of a smaller fresh acid dosage and longer use of the acid.

The feature of subjecting a solution of olefin in sulfuric acid to contact with a substantially olefin-free low-boiling isoparaffin to strip absorbed olefin product from the acid, and then passing the resulting mixture of isoparaffin and stripped olefin product to an alkylation reaction zone where the olefin product is alkylated by the isoparaffin in the presence of an alkylation catalyst is disclosed and claimed in copending application, Serial No. 392,874, filed May 10, 1941.

The feature of prediluting the olefin feed to an alkylation reaction zone with separated hydrocarbon phase or alkylate containing a high proportion of isoparaffins prior to contacting the olefin with the alkylation catalyst is disclosed and claimed in copending application, Serial No. 392,396, filed May 7, 1941.

Obviously many modifications and variations of the invention, as hereinbefore set forth, may be made without departing from the spirit and scope thereof, and therefore only such limitations should be imposed as are indicated in the appended claims.

We claim:

1. A process for the alkylation of isoparaffins with olefins, which comprises treating olefins and an excess of low boiling isoparaffins with strong sulfuric acid, whereby the isoparaffins are alkylated by the olefins, separating the used acid from the reaction products, separately contacting at least a portion of the used acid with substantially olefin-free isoparaffins to strip the acid of absorbed olefins, and passing the mixture of isoparaffins and hydrocarbons stripped from the acid to the alkylation operation.

2. A process for the alkylation of isoparaffins with olefins, which comprises passing strong sulfuric acid and low boiling isoparaffins serially through a multiple stage reaction zone, introducing the olefins in portions into a plurality of said stages, separating the used acid from the reaction products, separately contacting said used acid with substantially olefin-free isoparaffin charging stock to strip the acid of absorbed olefinic hydrocarbons, and passing the isoparaffin charging stock and hydrocarbons stripped from the acid to the alkylation operation.

3. A process according to claim 2 in which the flow of the acid and isoparaffins is concurrent.

4. A process according to claim 2 in which the flow of the acid and isoparaffins is countercurrent.

5. In the alkylation of an isoparaffin with an olefin in the presence of concentrated sulfuric acid, the improvement which comprises agitating used alkylation acid with a substantially olefin-free isoparaffin to recover absorbed olefin product from the acid to thereby produce an additional quantity of alkylate resulting from the alkylation of the olefin product stripped from the acid by the isoparaffin.

6. In a process for the alkylation of a low-boiling isoparaffin with an olefin, wherein the isoparaffin is contacted with the olefin in the presence of strong sulfuric acid under alkylating conditions in a reaction zone, reaction products are removed to a settling zone where hydrocarbon phase is separated from acid phase, and at least a portion of the separated acid is recycled to the said reaction zone, the improvement which comprises contacting the said recycle acid prior to its return to the said reaction zone with a substantially olefin-free low-boiling isoparaffin to strip absorbed olefin product therefrom, separating the said isoparaffin with stripped olefin product from the treated acid, and then passing the treated acid to the alkylation reaction zone.

7. The method according to claim 6, in which the low-boiling isoparaffin which is contacted with the recycle acid is isobutane.

ARTHUR R. GOLDSBY.
ERNEST F. PEVERE.
LOUIS A. CLARKE.
GEORGE B. HATCH.